United States Patent [19]
Padilla

[11] 3,968,334
[45] July 6, 1976

[54] AUDIOMETRIC METHOD AND APPARATUS FOR TESTING THE EFFECTIVENESS OF HEARING PROTECTIVE DEVICES

[76] Inventor: Miguel Padilla, 1830 Avenida del Mundo, No. 1712, Coronada, Calif. 92118

[22] Filed: Oct. 10, 1974

[21] Appl. No.: 513,604

[52] U.S. Cl. ............................ 179/175; 179/1 N; 179/156 R
[51] Int. Cl.² ........................................ H04R 29/00
[58] Field of Search ............ 179/175.1 A, 1 N, 1 P, 179/156 R, 184, 175; 181/130, 129

[56] References Cited
UNITED STATES PATENTS

| | | | |
|---|---|---|---|
| 2,946,862 | 7/1960 | Wadsworth | 179/156 R |
| 3,306,991 | 2/1967 | Wood | 179/156 R |
| 3,415,246 | 12/1968 | Hill | 181/130 |
| 3,536,835 | 10/1970 | Rawls et al. | 179/1 N |
| 3,602,329 | 8/1971 | Bauer | 181/129 |
| 3,621,488 | 11/1971 | Gales | 181/129 |
| 3,683,130 | 8/1972 | Kahn | 179/1 P |
| 3,729,598 | 4/1973 | Tegt et al. | 179/175.1 A |
| 3,787,899 | 1/1974 | Krawagna | 179/156 R |

Primary Examiner—Douglas W. Olms
Attorney, Agent, or Firm—R. S. Sciascia; G. J. Rubens

[57] ABSTRACT

A novel method and apparatus is disclosed for audiometrically testing the effectiveness and fitting of insert-type hearing protective devices whereby each ear is enclosed in a separate and portable audiometric enclosure having a telephonic earphone arrangement, the interior of each enclosure being freely spaced from the respective pinna of the ear to avoid any physical contact therebetween that may otherwise distort the ear canal supporting the protective device to be tested. Predetermined audiometric signals may be transmitted to each ear separately, both with and without the protective device, to obtain the difference of hearing thresholds and thereby determine separately, if needed, the fitting of each protective device, and its "real ear attenuation".

6 Claims, 2 Drawing Figures

AUDIOMETRIC METHOD AND APPARATUS FOR TESTING THE EFFECTIVENESS OF HEARING PROTECTIVE DEVICES

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

This invention relates to hearing protective devices, such as ear plugs, and more particularly to an audiometric method and portable apparatus for testing in a field environment the noise attenuation and fitting of insert type of hearing protective devices fitted in the external ear canals.

The use of hearing protective devices, such as earmuffs and insert-type ear plugs or the like, are required by the Occupational Safety and Health Act of 1970 as a safety measure in the noise hazardous areas present in many industrial plants to prevent permanent hearing loss. In most instances, insert-type ear plugs are employed because of their light weight, compactness, and overall convenience. However, because ear canals vary considerably in size and shape, from ear to ear and from individual to individual it is difficult to obtain an effective fit. Standard ear plugs are ideally conceived and designed to fit a canal resembling the shape of a cylinder, not that of a cone or a squashed banana as the case may be. Yet in the field one finds all sorts of odd shapes and sizes of ear canals, some of which are difficult or impossible to fit with standard insert-type plugs. Even when the ear canals are custom fitted with ear plugs by professional audiology technicians, the real ear attenuation may fall below the predetermined standards, in the order of at least 20 dB across the sound spectrum.

Unfortunately, the conventional method of testing ear plugs for effectiveness and fitting described in American National Standard Institute (ANSI) standard Z24.22 requires the use of a research-type installation which is large and complicated, such as an anechoic chamber, is so costly that few activities can afford them solely for audiometric purposes. In addition it utilizes a common free field condition for both ears, being impossible to determine which one of the two ear plugs is defective. Furthermore, when the anechoic, or approved type test chamber is employed the head of the subject being tested must be held in a fixed position because of ear-to-speaker distance problems and other variables.

Persons working in noisy environments are psychologically adjusted to the noise so that they are mentally unaware of the danger of being exposed to the noise at the expense of their cochlea in the inner ear mechanism. Because of the lack of convenient and readily portable test apparatus, hearing losses caused by the false security of wearing an inadequately fitted ear plug in noise hazardous areas, the average hearing compensation claim in a U.S. Navy installation, for example amounts to $18,000.

Although earmuffs have been used for a different purpose, namely an absolute test of hearing, such as represented by U.S. Pat. No. 3,220,505, this type of earmuff is entirely unsuitable for the relative testing of ear plugs because the earmuffs are required, and constructed, to hug the ear tightly. Although the physical distortion of the ear canal caused by the earmuff in this patented device is not disadvantageous for reasons heretofore described it is critical for the purpose of the present invention.

SUMMARY OF THE INVENTION

An inexpensive, simple and versatile method and apparatus is provided for testing the fitting and general effectiveness of insert-type hearing protective devices, which method can be carried out in a small quiet area of any field installation, as well as in an industrial audiometer booth.

The apparatus utilized in the novel method comprises a pair of earmuffs readily supportable on the subjects head to enclose both ears and without requiring the movement of the head to be restricted. It is important that the novel earmuffs be designed so that when mounted on the head, the respective ear has complete freedom therein. That is, the pinna of the ear must be spaced from the interior of the muff to prevent physical contact that may otherwise distort the ear canal in which the ear plug to be tested has been inserted.

Each earmuff contains an earphone to which can be transmitted individually to each earmuff, predetermined signals from a standard audiometer of other audiometric source such as pure tones, "pink" noise or narrowband sound. By individual testing each ear individually, there can be no problem of ascertaining which of the two ear plugs is defectively fitted.

In carrying out the invention method, the subject is preferrably positioned in a quiet area, such as an industrial audiometer booth, or room. After the earmuffs are mounted on the subject's head, with each ear being covered by a separate earmuff, predetermined audiometric signals are transmitted to each ear jointly or independently. As this test is a relative measure of hearing, as distinguished from an absolute test of hearing per se, the series of transmitted signals are repeated both without and with the ear plugs installed in the ears to obtain the relative difference between the two hearing thresholds.

STATEMENT OF THE OBJECTS OF THE INVENTION

A principal object of this invention is to provide a simple, inexpensive, and reliable method and apparatus for testing the fitting and general effectiveness of insert-type hearing protective devices.

Another important object is to provide portable apparatus so that the method can be conducted in any quiet area available in most industrial facilities.

Still another object is to provide such a method which produces the relative hearing threshold values of each ear independently, or jointly, both with and without the presence of the hearing protective device, so that the difference in hearing thresholds can be obtained, or real ear attenuation of the plug in question.

Other objects, advantages and novel features of the invention will become apparent from the following detailed description of the invention when considered in conjunction with the accompanying drawings.

BRIEF DESCRIPTION OF THE DRAWINGS

FIG. 2 is an enlarged cross-sectional view of one of the earmuffs mounted to the user's head, showing the

DESCRIPTION OF THE PREFERRED EMBODIMENTS

Figure 1:
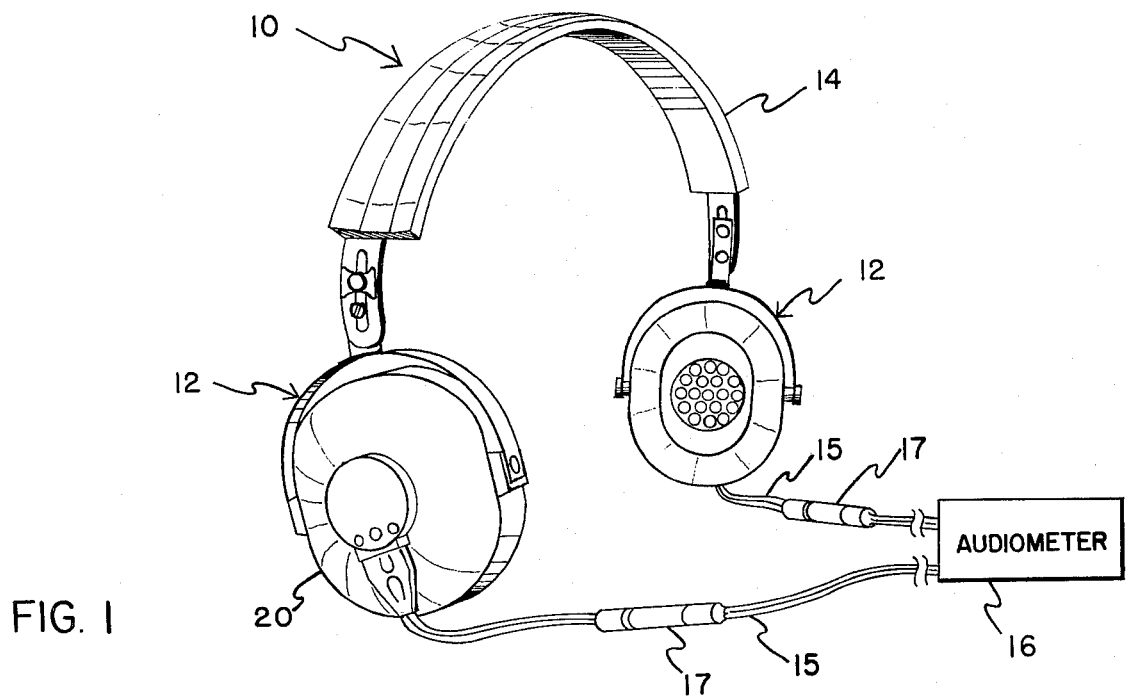
FIG. 1 is a perspective view of the pair of test earmuffs individually connected to an audiometer.

Referring to the drawings where like reference numerals refer to similar parts throughout the figures there is shown in FIG. 1 a headset 10 comprising a pair of earmuffs 12, one for each of the ears of the subject S, and connected together by an adjustable, spring-biased headband 14. It is important for reasons later to be described, that each earmuff be independently connected by cords 15 to a conventional audiometer 16 via quick-disconnect jacks 17, so that each ear can be tested jointly or individually, should only one of the ear plugs be suspect of being defectively fitted.

Figure 2:
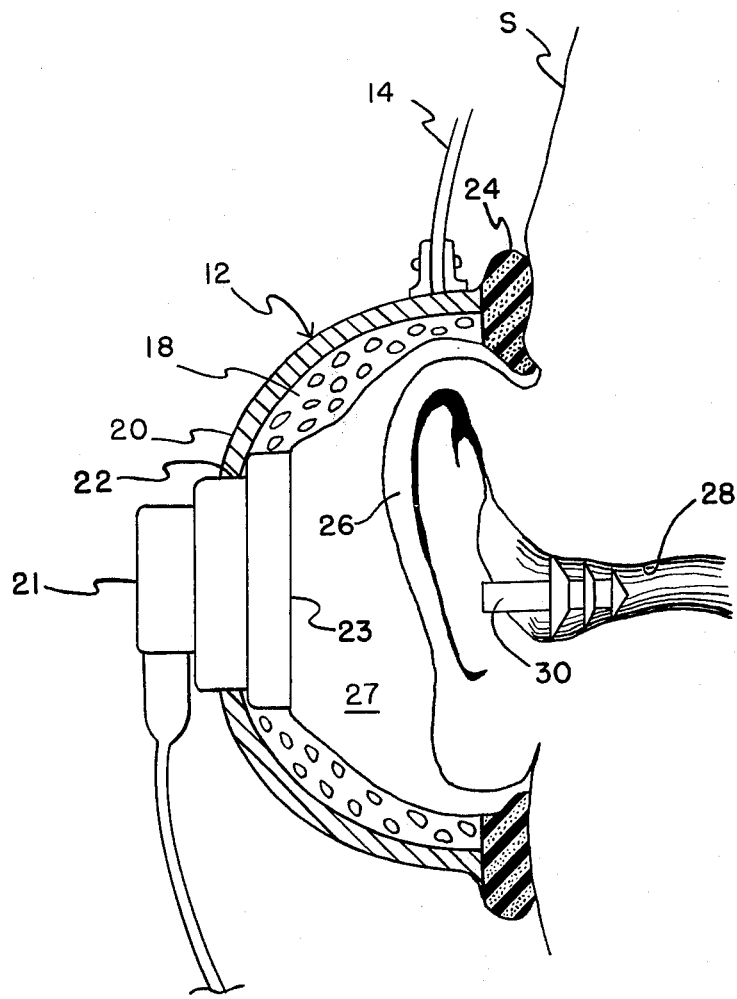

As best shown in FIG. 2, each earmuff functions essentially as a small portable anechoic chamber. Although it is within the scope of this invention that the earmuffs can be custom designed and manufactured, as a practical matter it has been found convenient and inexpensive to modify a David Clark commercial model 19A Circumaural Hearing Protector, Federal Stock No. 4240-759-3290, because this protector so happens to have a very deep cup shape that is required to carry out the invention process. The description will be limited to the single earmuff illustrated in FIG. 2, although it is to be understood that the description applies equally to both earmuffs of the headset.

With the noise-absorbing pad 18 removed, each earmuff cup 20 is drilled in the center with a hole 4.35 cm in diameter. Pad 18 is then reintroduced in the cup, and with a surgical blade a round hole 22 is cut therein the same size as the drilled hole in the cup. The pad is again removed from the cup and a suitable standard telephonic earphone 21 is securely epoxied to the cup with the earphone face 23 inside and the electric cord outside the cup. After the epoxy has hardened, absorbing pad 18 is then reinstalled and carefully adhesively secured around the back of the earphone faces.

The earmuff is provided with a foam rubber peripheral lip 24, which by the spring action of headband 14, sealably engages the head of the wearer and provides a barrier to outside noises. When thus mounted, the entire ear pinna 26 is freely spaced from the interior of the earmuff, which is an important and necessary feature of this invention for preventing distortion of the ear canal 28 in which ear plug 30 is installed. By insuring that there is no physical contact between ear pinna and the earmuff an adequate free space 27 is made available which enables the earmuff to function, in effect, as a miniature anechoic chamber having the additional features of being portable and extremely simple in construction and in use. The free space 27 normally should have a volumetric displacement of approximately no less than 300 cubic centimeters.

The invention method is carried out in a relatively quiet area. Because this test is a relative test, as distinguished from an absolute hearing test, the threshold values are obtained under two conditions, namely, with the ear plugs installed and with the ear plugs removed. The earmuffs carefully attached to the head so that the respective ears are freely positioned in the earmuffs, and the muff is sealed to the head through peripheral lip 24. The subject's head is not restricted in movement.

For all practical purposes, the testing can be conducted with a pure tone signal, using one or two frequencies at the low end of the sound spectrum where the real ear attenuation of ear plugs is most difficult to achieve. It is commonly accepted that real ear attenuation of an ear plug tends to increase with an increase with frequency. However, the method admits of the use of a variety of types of signals, when compared to the prior art method requiring the use of a research type of fixed anechoic installation. The earmuffs are arranged with the audiometer so that both of the ear plugs can be tested simultaneously or individually.

Obviously many modifications and variations of the present invention are possible in the light of the above teachings. It is therefore to be understood that within the scope of the appended claims the invention may be practiced otherwise than as specifically described.

What is claimed is:

1. An audiometric method for testing the effectiveness of insert-type hearing protective devices in a user's ear canals comprising the steps of:
    enclosing each ear with a separate portable acoustical enclosure;
    positioning the enclosure so that each ear pinna is freely spaced from the respective enclosure to avoid distortion of the ear canals by physical contact therewith,
    attaching and sealing the enclosures to the user's head to provide a free field condition for each ear without the need to restrict movement of the head,
    applying predeterimed audiometric signals to each of said ears within the enclosures in two conditions, namely with the protective devices removed and with the protective devices present,
    ascertaining the user's hearing threshold levels in both conditions to determine the relative noise attenuation of the protective devices.

2. The audiometric method of claim 1 wherein the predetermined signals are of a pure tone.

3. The audiometric method of claim 1 wherein the predetermined signals are of a "pink" noise tone.

4. The audiometric method of claim 1 wherein the predetermined signals are of a narrowband sound.

5. The audiometric method of claim 1 wherein the predetermined signals are introduced to each ear separately.

6. A headset for testing audiometrically the effectiveness of insert-type hearing protective devices in a user's ear canals comprising:
    a pair of ear enclosures, one for each ear;
    each enclosure comprising an outer shell;
    resilient means disposed about the periphery of each enclosure for sealably engaging the head of the user around the respective ear;
    a telephonic earphone centrally mounted in each enclosure;
    each of said outer shells having an annular space between the earphone and the resilient means provided with sound-absorbing acoustical material;
    each of said enclosures including earphone, resilient means and acoustical material all being spaced from the pinna of the ear to avoid physical distortion of the ear canals and to provide a free space volume of no less than 300 cubic centimeters; and
    means for connecting each of said earphones to a suitable sound source to enable each ear to be tested separately or together.

* * * * *